US00PP33123P2

(12) United States Plant Patent
Boxriker

(10) Patent No.: US PP33,123 P2
(45) Date of Patent: Jun. 1, 2021

(54) ***OSTEOSPERMUM* PLANT NAMED 'KLEOE19400'**

(50) Latin Name: ***Osteospermum ecklonis* Norl**
Varietal Denomination: KLEOE19400

(71) Applicant: Klemm+Sohn GmbH & Co. KG, Stuttgart (DE)

(72) Inventor: Maike Boxriker, Schwäbisch Gmünd (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/868,174

(22) Filed: May 6, 2020

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 6/148; A01H 5/02
See application file for complete search history.

*Primary Examiner* — Keith O. Robinson
(74) *Attorney, Agent, or Firm* — Weatherly IP Solutions, LLC; James Weatherly

(57) ABSTRACT

A new *Osteospermum* plant particularly distinguished by having orange flowers, a very early flowering time and a semi-upright plant habit.

1 Drawing Sheet

Genus and species: *Osteospermum ecklonis* Norl.
Variety denomination: 'KLEOE19400'.

BACKGROUND OF THE NEW PLANT

The present invention comprises a new and distinct variety of *Osteospermum*, botanically known as *Osteospermum ecklonis* Norl, and hereinafter referred to by the variety name 'KLEOE19400'. 'KLEOE19400' originated from a cross-pollination between the proprietary female *Osteospermum* variety 'OE-2013-0095' (unpatented), and the male *Osteospermum* variety 'KLEOE14243' (U.S. Plant Pat. No. 27,344).

In the summer of 2015, the two *Osteospermum* parental lines 'OE-2013-0095' and 'KLEOE14243' were crossed in Nairobi, Kenya, and seeds were obtained. The seeds were sown and plants were grown for evaluation. The seedling was selected in spring 2016 and named 'KLEOE19400'. In fall of 2016, 'KLEOE19400' was first vegetatively propagated by vegetative cuttings in Stuttgart, Germany. 'KLEOE19400' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Orange flower color;
2. A very early flowering time; and
3. Semi-upright habit.

DESCRIPTION OF THE PHOTOGRAPH

This new *Osteospermum* plant is illustrated by the accompanying photograph, which shows the plant with flowers grown in a pot. The photograph is of an eleven-week-old plant grown in a controlled greenhouse environment in Stuttgart, Germany in May 2018. The colors shown are as true as can be reasonably obtained by conventional photographic procedures.

DESCRIPTION OF THE NEW VARIETY

The following detailed descriptions set forth the distinctive characteristics of 'KLEOE19400'. The data which define these characteristics were collected from asexual reproductions carried out in Latina, Italy. Data was collected on nineteen-week-old plants grown in a controlled greenhouse environment in Latina, Italy under greenhouse conditions in February 2020. Color references are to The R.H.S. Colour Chart of The Royal Horticultural Society of London (R.H.S.), 5$^{th}$ edition (2007).

Classification:
- *Family*.—Compositae.
- *Botanical*.—*Osteospermum ecklonis* Norl.
- *Common*.—*Osteospermum*, African Daisy.
- *Designation*.—'KLEOE19400'.

Parentage:
- *Female parent*.—*Osteospermum* line 'OE-2013-0095' (unpatented).
- *Male parent*.—*Osteospermum* line 'KLEOE14243' (U.S. Plant Pat. No. 27,344).

Plant:
- *Form and habit*.—Herbaceous perennial, but usually cultivated as an annual; not frost resistant.
- *Growth habit*.—Upright.
- *Branching habit*.—Freely branching.
- *Height (from top of soil, including inflorescence)*.—30.0 cm.
- *Width (including inflorescences)*.—38.0 cm.
- *Propagation*.—Vegetative cuttings.
- *Time to produce a finished flowering plant*.—9 weeks.
- *Time to initiate and develop roots*.—5 weeks.
- *Root description*.—Fine; white (RHS 155A).

Leaves:
*Arrangement*.—Alternate.
*Shape*.—Obovate.
*Apex*.—Acute.
*Base*.—Acute.
*Margin*.—Entire.
*Immature color*.—Upper surface: RHS 137B. Lower surface: RHS 137C.
*Mature color*.—Upper surface: RHS 146A. Lower surface: RHS 146C.
*Length*.—7.7 cm.
*Width*.—2.2 cm.
*Texture*.—Upper surface: Leathery. Lower surface: Leathery smooth, covered with fine hairs.
*Petioles*.—Absent.
*Venation pattern*.—Pinnate.
*Venation color*.—Upper surface: RHS 144A. Lower surface: RHS N144C.

Stems:
*Total number of branches per plant* (*calculated at the base of the plant*).—5.
*Length*.—38.0 cm.
*Diameter*.—0.5 cm.
*Internode length*.—1.5 cm.
*Color*.—RHS 144A.
*Texture*.—Smooth.
*Anthocyanin*.—Absent.

Buds:
*Shape*.—Round to ovoid.
*Length*.—0.9 cm.
*Diameter*.—1.0 cm.
*Color* (*at tight bud just before the ray florets unfold*) .—RHS 144A.

Inflorescence:
*Type*.—Composite, single.
*Blooming habit*.—Semi-upright, with long flower stems.
*Quantity of inflorescences per plant*.—7.
*Lastingness of the inflorescences on the plant*.—10 to 15 days.
*Fragrance*.—Present; sweet.
*Inflorescence diameter*.—6.8 cm.
*Inflorescence depth*.—1.0 cm.
*Disc diameter*.—1.7 cm.

Disc floret:
*Quantity per inflorescence*.—About 120.
*Shape*.—Tubular.
*Tube color*.—RHS 157A.
*Length*.—1.2 cm.
*Diameter* (*at apex*).—0.2 cm.
*Apex*.—Acute.
*Apex color*.—RHS N77A.
*Base*.—Acute.
*Base color*.—RHS N167D.
*Margin*.—Entire.

Ray floret:
*Quantity per inflorescence*.—21.
*Shape*.—Oblanceolate.
*Color*.—Upper surface: RHS 17A. Lower surface: RHS 163A.
*Length*.—3.0 cm.
*Width*.—1.0 cm.
*Apex*.—Acute.
*Base*.—Acute.
*Margin*.—Entire.
*Texture*.—Upper and lower surfaces: Smooth.
*Peduncle*.—Length: 12.0 cm. Diameter: 0.2 cm. Texture: Smooth with hairs. Color: RHS 144A.

Phyllaries:
*Texture*.—Smooth with fine hairs.
*Color*.—RHS 144A.
*Arrangement*.—Single.
*Observed quantity per plant*.—20.
*Shape*.—Lanceolate.
*Color*.—Upper surface: RHS 144A. Lower surface: RHS 145A.
*Length*.—1.2 cm.
*Width*.—0.2 cm.
*Apex*.—Acute.
*Base*.—Obtuse.
*Margin*.—Entire.
*Texture*.—Upper surface: Smooth with fine hairs. Lower surface: Smooth.

Reproductive organs:
*Androecium*.—Location: On the disc floret. Stamens: Quantity: Around 50. Shape: Filamentous. Filament length: 0.6 cm. Filament diameter: Less than 0.1 cm. Anther: Shape: Lanceolate. Color: RHS 83A. Length: Less than 0.1 cm. Diameter: Less than 0.1 cm. Pollen: Color: RHS N172A. Amount: Moderate.
*Gynoecium*.—Location: On the base of the petals (ray floret) and reduced on disc florets. Pistils: Number: Around 50. Length: 0.3 cm. Diameter: Less than 0.1 cm. Stigma: Color: RHS 72A. Shape: Filamentous. Length: 0.2 cm. Diameter: Less than 0.1 cm. Style: Color: RHS N72A. Length: 0.1 cm. Diameter: Less than 0.1 cm.

Fruit and seed set: None observed.

Disease and pest/insect resistance: No particular disease or insect resistance observed.

COMPARISON WITH PARENTAL LINES AND KNOWN VARIETY

'KLEOE19400' is distinguished from its parents as described in Table 1:

TABLE 1

Comparison with Parental Lines

| Trait | Variety 'KLEOE19400' | Female parent 'OE-2013-0095' | Male Parent 'KLEOE14243' |
|---|---|---|---|
| Flower color | Orange | Red-Orange | Yellow |

'KLEOE19400' is most similar to the *Osteospermum* plant named 'KLEOE12197' (Not patented). Differences between the two varieties are described in Table 2:

TABLE 2

Comparison with Similar Variety

| Trait | Variety 'KLEOE19400' | Commercial line 'KLEOE12197' |
|---|---|---|
| Flower Color | Orange | Pink |
| Flowering time | Very early | Early |
| Habit | Semi-upright | Upright |

I claim:

1. A new and distinct cultivar of *Osteospermum* Plant Named 'KLEOE19400' as described and illustrated herein.

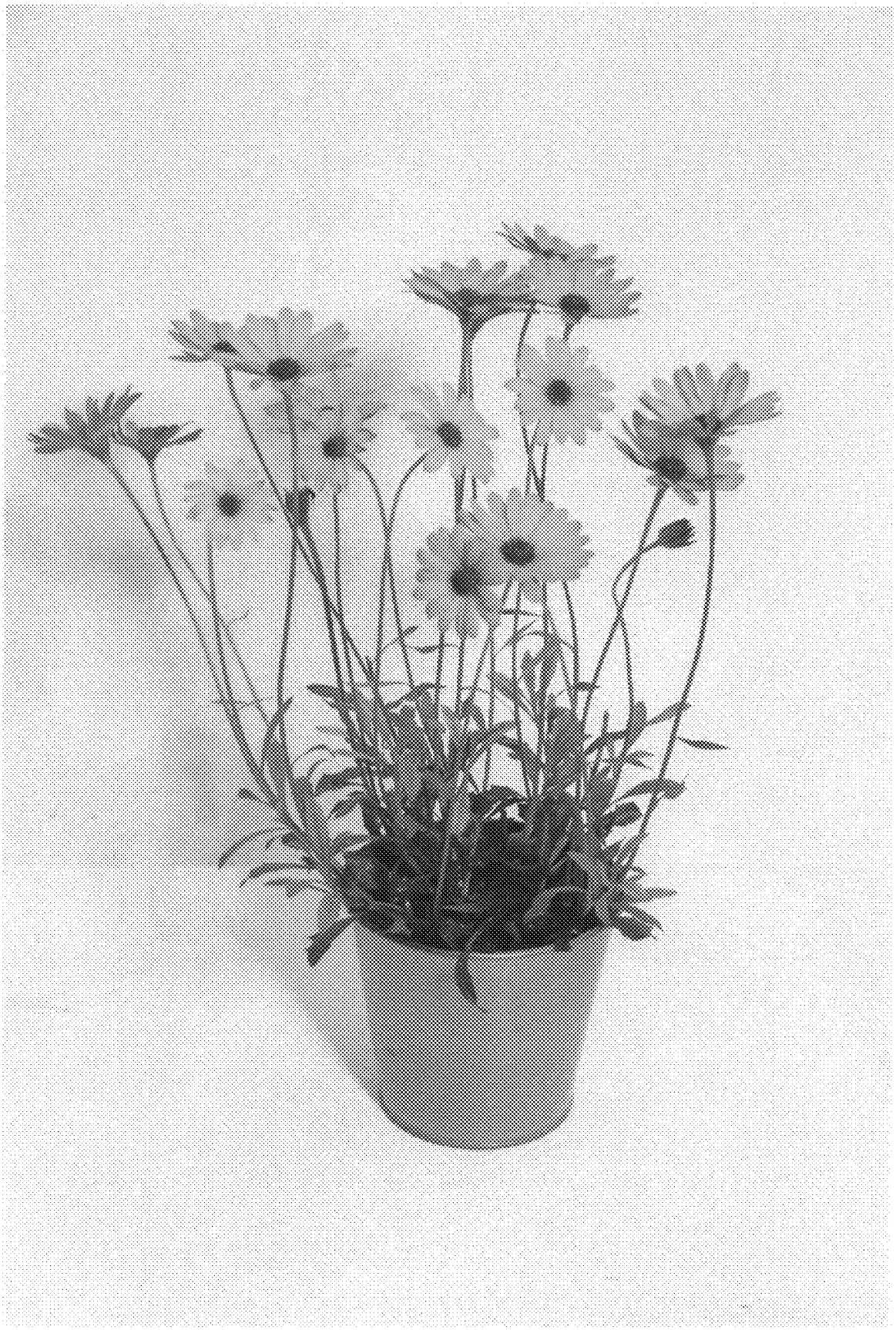

* * * * *